(12) United States Patent
Hwang et al.

(10) Patent No.: US 9,895,329 B1
(45) Date of Patent: Feb. 20, 2018

(54) FORMYL PEPTIDE RECEPTOR 1 ANTAGONISTS AND USES THEREOF

(71) Applicant: Chang Gung University, Taoyuan (TW)

(72) Inventors: Tsong-Long Hwang, Taoyuan (TW); Yung-Fong Tsai, Taoyuan (TW); Chun-Yu Chen, Taoyuan (TW); Liang-Mou Kuo, Chiayi County (TW); Yuan-Bin Cheng, Kaohsiung (TW); Chih-Hsin Wang, Kaohsiung (TW); Fang-Rong Chang, Kaohsiung (TW); Yang-Chang Wu, Taichung (TW)

( * ) Notice: Subject to any disclaimer, the term of this patent is extended or adjusted under 35 U.S.C. 154(b) by 0 days.

(21) Appl. No.: 15/393,239

(22) Filed: Dec. 28, 2016

(51) Int. Cl.
*A61K 31/194* (2006.01)

(52) U.S. Cl.
CPC .................................. *A61K 31/194* (2013.01)

(58) Field of Classification Search
None
See application file for complete search history.

(56) References Cited

PUBLICATIONS

Chang, F.R. et al., Planta Medica 2016 vol. 82 (S 01) S1-S381.*
Yoshizumi, K. et al., J. Ag Food Chem. 2006, vol. 54, pp. 335-341.*
(ALB Technology online catalog page, www.albmaterials.com, accessed Jun. 19, 2017.*
www.nutragin.com, accessed Jun. 19, 2017.*

* cited by examiner

*Primary Examiner* — Heidi Reese (57) ABSTRACT

Disclosed herein are novel formyl peptide receptor 1 (FPR1) antagonists and their uses in manufacturing medicaments for the treatment and/or prophylaxis of diseases and/or disorders mediated by FPR1.

3 Claims, 4 Drawing Sheets

FORMYL PEPTIDE RECEPTOR 1 ANTAGONISTS AND USES THEREOF

BACKGROUND OF THE INVENTION

1. Field of the Invention

The present disclosure in general relates to the field of formyl peptide receptor 1 (FPR1); more particularly to the antagonists of FPR1, and their uses in the treatment or prophylaxis of diseases and/or disorders mediated by FPR1.

2. Description of Related Art

The receptor for the N-methyl methionine containing peptides is known as the formyl peptide receptor (FPR), which is a G protein coupled receptor (GPCR) expressed specifically on neutrophils, eosinophils, and basophils (i.e., granulocytes). In humans, there are three isoforms of FPR, they are FPR1, FPR2, and FPR3. Although formyl-L-methionyl-L-leucyl-L-phenylalanine (MILS) mediated chemoattraction is among the best known and characterized immunomodulatory signaling systems, little is known about the in vivo contribution of FPR signaling relative to other chemoattractants, including various components of the complement system and many known chemokines, in various physiological scenarios of both health and disease. This is especially true of FPR signaling might play in human disease and disorders, especially in acute or chronic inflammation. The potential of the FPR as the target for anti-inflammatory therapy is largely unexplored, and FPR antagonists may be of considerable interest for use in treatment of a variety of inflammation-related disorders.

Therefore, there is an unmet medical need for new therapeutic agents acting through FPR signaling, for the treatment and/or prophylaxis of inflammation-related diseases and/or disorders.

SUMMARY

The present disclosure is based on unexpected discovery that certain compound isolated from *L. synbalanos* is a potent formyl peptide receptor (FPR) modulator, particularly formyl peptide receptor 1 (FPR1) modulator that bind to FPR1 and antagonizes the activation of FPR1 signaling, these compounds are thus useful as lead compounds for the development of medicaments for treating diseases and/or disorders mediated by FPR1, such as an immune disorder, an infectious disease, a cancer, a cardiovascular disease, or a trauma.

Accordingly, one aspect of the present disclosure is to provide a novel use of the compound having the structure of formula (I), for the manufacture of a medicament for treating diseases and/or disorders mediated by FPR1:

(I)

The present disclosure also encompasses a method for the treatment or prophylaxis of a subject having or suspected of having a disease and/or disorder mediated by FPR1. The method comprises the step of administering a therapeutically or prophylactically effective amount of the compound of formula (I) to the subject, so as to ameliorate, mitigate and/or prevent the symptoms of the disease and/or disorder mediated by FPR1.

According to embodiments of the present disclosure, the disease and/or disorder mediated by FPR1 may be an immune disorder, an infectious disease, a cancer, a cardiovascular disease, or a trauma.

Examples of the immune disorder treatable by the present method include, but are not limited to, eczema, dermatitis, psoriasis, an allergic disorder, acute respiratory distress syndrome, and chronic obstructive pulmonary disease (COPD). Examples of allergic disorder treatable by the present method include, but are not limited to, asthma, hay fever, hypereosinophilic syndrome, rheumatoid arthritis, and an eosinophil-associated gastrointestinal disorder. Examples of the eosinophil-associated gastrointestinal disorder that may be treated by the present method include, but are not limited to, eosinophilic gastroenteritis, allergic colitis, eosinophilic esophagitis, inflammatory bowel disease (IBS) and gastrointestinal reflux disease.

Examples of the infectious disease treatable by the present method include, but are not limited to, bacterial, fungal or viral infections, sepsis, and septic shock. In one preferred example, the infectious disease treatable by the present method is sepsis.

Examples of the cancer treatable by the present method include, but are not limited to, Hodgkin's disease, Non-Hodgkin's lymphomas, Ewing's sarcoma, multiple myeloma, Wilms' tumor, bone tumors, neuroblastoma, retinoblastoma, testicular cancer, thyroid cancer, prostate cancer, larynx cancer, cervical cancer, nasopharynx cancer, breast cancer, colon cancer, pancreatic cancer, head and neck cancer, esophageal cancer, rectal cancer, small-cell lung cancer, non-small-cell lung cancer, brain cancer, melanoma, a non-melanoma skin cancer, and a CNS neoplasm.

Examples of the cardiovascular disease treatable by the present method include, but are not limited to, acute arterial thrombosis and embolism, arrhythmias, atherosclerosis, chronic peripheral arterial occlusive disease (PAOD), hypertension, inflammatory vascular disorders, myocardial infarction (MI), myocardial ischemia/reperfusion injury, Raynaud's phenomenon and venous disorders.

Example of the trauma treatable by the present method is hemorrhagic shock.

According to some embodiments of the present disclosure, the compound of formula (I) is administered to the subject in the amount of 0.01 to 100 mg/Kg.

According to preferred embodiments of the present disclosure, the subject is a human.

The details of one or more embodiments of this disclosure are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The accompanying drawings, which are incorporated in and constitute a part of the specification, illustrate various example systems, methods and other exemplified embodiments of various aspects of the invention. The present description will be better understood from the following detailed description read in light of the accompanying drawings, where.

DETAILED DESCRIPTION OF THE INVENTION

The detailed description provided below in connection with the appended drawings is intended as a description of the present disclosure and is not intended to represent the only forms in which the present disclosure may be constructed or utilized.

1. Definitions

Unless otherwise indicated, the term "effective amount" as referred to herein designate the quantity of a compound which is sufficient to yield a desired response. For therapeutic purposes, the effective amount is also one in which any toxic or detrimental effects of the compound are outweighed by the therapeutically beneficial effects. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/Kg). Alternatively, the effective amount can be expressed in the concentration of the active component (e.g., compound LS-PH of the present disclosure), such as molar concentration, mass concentration, volume concentration, molality, mole fraction, mass fraction and mixing ratio. Further, persons having ordinary skills in the related art could calculate the human equivalent dose (HED) for the medicament (such as the compound of the present disclosure) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

Unless otherwise indicated, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound is an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, a "prophylactically effective amount" of a compound is an amount sufficient to prevent a disease or condition, or one or more symptoms associated with the disease or condition, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Unless otherwise indicated, the terms "treat," "treating" and "treatment" contemplate an action that occurs while a patient is suffering from the specified disease or disorder, which reduces the severity of the disease or disorder, or one or more of its symptoms, or retards or slows the progression of the disease or disorder.

The term "subject" or "patient" is used interchangeably herein and is intended to mean a mammal including the human species that is treatable by the compound of the present invention. The term "mammal" refers to all members of the class Mammalia, including humans, primates, domestic and farm animals, such as rabbit, pig, sheep, and cattle; as well as zoo, sports or pet animals; and rodents, such as mouse and rat. Further, the term "subject" or "patient" intended to refer to both the male and female gender unless one gender is specifically indicated. Accordingly, the term "subject" or "patient" comprises any mammal which may benefit from the treatment method of the present disclosure. Examples of a "subject" or "patient" include, but are not limited to, a human, rat, mouse, guinea pig, monkey, pig, goat, cow, horse, dog, cat, bird and fowl. In a preferred embodiment, the subject is a human.

It should also be noted that if the stereochemistry of a structure or a portion of a structure is not indicated with, for example, bold or dashed lines, the structure or the portion of the structure is to be interpreted as encompassing all stereoisomers of it. Similarly, names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context clearly dictates otherwise.

2. Methods of Treatment

Inventors of the present disclosure unexpectedly identify certain compounds isolated from *L. synbalanos* are potent formyl peptide receptor (FPR) modulator, particularly, formyl peptide receptor 1 (FPR1) modulator. It was found that the compounds of the present disclosure may bind to FPR1 and antagonize the activation of FPR1 signaling, these compounds are thus useful as lead compounds for the development of medicaments for treating diseases and/or disorders mediated by FPR1.

The present invention thus is directed to the therapeutic use of FPR1 antagonists for the treatment or prophylaxis of diseases and/or disorders mediated by FPR1, such as immune disorders, infectious diseases, cancers, cardiovascular diseases, and traumas.

The present invention thus encompasses a method for the treatment or prophylaxis of a subject having or suspected of having a disease and/or disorder mediated by FPR1. The method comprises the step of administering a therapeutically or prophylactically effective amount of the compound of formula (I) of the present disclosure to the subject, so as to ameliorates, mitigates and/or prevents the symptoms of the disease and/or disorder mediated by FPR1:

(I)

The compound of formula (I) of the present disclosure may be isolated from leaves and/or stems of *L. synbalanos* in accordance with process set forth in the working examples of the present disclosure. Further, the compound of formula (I) of the present disclosure contain one or more stereocenters, thus can exist as racemic mixtures of enantiomers or mixtures of diastereomers. This invention thus encompasses stereomerically pure forms of such compounds, as well as mixtures of those forms. Stereoisomers may be asymmetrically synthesized or resolved using standard techniques such as crystallization, chromatography, and the use of a resolving agent. One preferred way of separating enantiomers from a racemic mixture is by use of preparative high performance liquid chromatography (HPLC). Alternatively, the racemic may be separated into its enantiomers by reacting with an optically active form of a resolving agent in the presence of a solvent. Depending on the optical form of the resolving agent, one of the two enantiomers is separated out as an insoluble salt with high yield and high optical purity, while the opposite enantiomer remains in the solution.

The present invention thus further encompasses stereoisomeric mixtures of compounds disclosed herein. It also encompasses configurational isomers of compounds disclosed herein (e.g., cis and trans isomers, whether or not involving double bonds), either in admixture or in pure or substantially pure form.

According to embodiments of the present disclosure, the disease and/or disorder mediated by FPR1 may be an immune disorder, an infectious disease, a cancer, a cardiovascular disease, or a trauma.

According to some embodiments of the present disclosure, examples of the immune disorder treatable by the present method include, but are not limited to, eczema, dermatitis, psoriasis, an allergic disorder, acute respiratory distress syndrome, and chronic obstructive pulmonary disease (COPD). Examples of allergic disorder treatable by the present method include, but are not limited to, asthma, hay fever, hypereosinophilic syndrome, rheumatoid arthritis, and an eosinophil-associated gastrointestinal disorder. Examples of the eosinophil-associated gastrointestinal disorder that may be treated by the present method include, but are not limited to, eosinophilic gastroenteritis, allergic colitis, eosinophilic esophagitis, inflammatory bowel disease (IBS) and gastrointestinal reflux disease.

According to some embodiments of the present disclosure, examples of the infectious disease treatable by the present method include, but are not limited to, bacterial, fungal or viral infections, sepsis, and septic shock. In one preferred example, the infectious disease treatable by the present method is sepsis.

According to some embodiments of the present disclosure, examples of the cancer treatable by the present method include, but are not limited to, Hodgkin's disease, Non-Hodgkin's lymphomas, Ewing's sarcoma, multiple myeloma, Wilms' tumor, bone tumors, neuroblastoma, retinoblastoma, testicular cancer, thyroid cancer, prostate cancer, larynx cancer, cervical cancer, nasopharynx cancer, breast cancer, colon cancer, pancreatic cancer, head and neck cancer, esophageal cancer, rectal cancer, small-cell lung cancer, non-small-cell lung cancer, brain cancer, melanoma, a non-melanoma skin cancer, and a CNS neoplasm.

According to some embodiments of the present disclosure, examples of the cardiovascular disease treatable by the present method include, but are not limited to, acute arterial thrombosis and embolism, arrhythmias, atherosclerosis, chronic peripheral arterial occlusive disease (PAOD), hypertension, inflammatory vascular disorders, myocardial infarction (MI), myocardial ischemia/reperfusion injury, Raynaud's phenomenon and venous disorders.

According to some embodiments of the present disclosure, specific example of the trauma treatable by the present method is hemorrhagic shock.

Other existing treatments of such disease and/or disorders may also be used along with the present treatment. Accordingly, the present invention also encompasses administering another therapeutic agent conventionally used to treat FPR1-mediated diseases and/or disorders, before, together with, or after the administration of the compound of formula (I). The therapeutic agent conventionally used to treat FPR1-mediated diseases and/or disorders may be a known FPR1 antagonist (e.g., cyclosporine A, cyclosporine H, and etc), an anti-inflammatory agent (e.g., steroid), an anti-biotic (e.g., penicillin), an anti-neoplasm agent, or a cardiovascular drug. For example, in the case of treating asthma, in addition to administering the compound of formula (I) to the asthma patient, the present method may further include administering any agent known to attenuate, reduce or alleviate the level of bronchoconstriction or bronchospasm associated with asthma attack.

According to embodiments of the present disclosure, the compound of formula (I) may be administered to the subject in the amount of about 0.01-100 mg/Kg, such as 0.01, 0.05, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 mg/Kg; preferably in the amount of about 0.1-90 mg/Kg, such as 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and 90 mg/Kg; more preferably in the amount of about 1-80 mg/Kg, such as 1.0, 2.0, 3.0, 4.0, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, and 80 mg/Kg.

The amount, route of administration and dosing schedule of the compound of formula (I) will depend upon factors such as the specific indication to be treated, prevented, or managed, and the age, sex and condition of the patient. The roles played by such factors are well known in the art, and may be accommodated by routine experimentation.

3. Pharmaceutical Formulation

This invention encompasses pharmaceutical compositions for the treatment or prophylaxis of a disease and/or disorder mediated by FPR1. The pharmaceutical composition comprises a therapeutically or prophylactic effective amount of a compound of formula (I) of the present invention, and a pharmaceutical acceptable excipient.

The compound of formula (I) is present at a level of about 0.1% to 99% by weight, based on the total weight of the pharmaceutical composition. In some embodiments, the compound of formula (I) is present at a level of at least 1% by weight, based on the total weight of the pharmaceutical composition. In certain embodiments, the compound of formula (I) is present at a level of at least 5% by weight, based on the total weight of the pharmaceutical composition. In still other embodiments, the compound of formula (I) is present at a level of at least 10% by weight, based on the total weight of the pharmaceutical composition. In still yet other embodiments, the compound of formula (I) is present at a level of at least 25% by weight, based on the total weight of the pharmaceutical composition.

In some embodiments, the pharmaceutical composition further comprises another FPR1 antagonist. According to another embodiment of the present disclosure, the pharmaceutical composition further comprises an anti-inflammatory agent. According to other embodiment of the present disclosure, the pharmaceutical composition may further comprise an anti-biotic. According to still another embodiment of the present disclosure, the pharmaceutical composition further comprises a cardiovascular drug. According to a further embodiment of the present disclosure, the pharmaceutical composition further comprises an anti-neoplasm agent.

Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intra-arterial), or transdermal administration to a patient. Examples of dosage forms include, but are not limited to: tablets; caplets; capsules, such as soft elastic gelatin capsules; cachets; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the compounds of this invention from degradation within the gastrointestinal tract. Similarly, a formulation may contain ingredients that facilitate delivery of the active ingredient(s) to the site of action. For example, compounds may be administered in liposomal formulations, in order to protect them from degradative enzymes, facilitate transport in circulatory system, and effect delivery across cell membranes to intracellular sites.

Similarly, poorly soluble compounds may be incorporated into liquid dosage forms (and dosage forms suitable for reconstitution) with the aid of solubilizing agents, emulsifiers and surfactants such as, but not limited to, cyclodextrins (e.g., α-cyclodextrin or β-cyclodextrin), and non-aqueous solvents, such as, but not limited to, ethyl alcohol, isopropyl alcohol, ethyl carbonate, ethyl acetate, benzyl alcohol, benzyl benzoate, propylene glycol, 1,3-butylene glycol, dimethyl formamide, dimethyl sulfoxide (DMSO), biocompatible oils (e.g., cottonseed, groundnut, corn, germ, olive, castor, and sesame oils), glycerol, tetrahydrofurfuryl alcohol, polyethylene glycols, fatty acid esters of sorbitan, and mixtures thereof (e.g., DMSO:corn oil).

The composition, shape, and type of a dosage form will vary depending on its use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

3.1 Oral Dosage Forms

Pharmaceutical compositions of the present invention suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See, e.g., *Remington's Pharmaceutical Sciences*, 18th ed., Mack Publishing, Easton Pa. (1990).

Typical oral dosage forms are prepared by combining the active ingredient(s) in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms. If desired, tablets can be coated by standard aqueous or non-aqueous techniques. In general, pharmaceutical compositions and dosage forms are prepared by uniformly and intimately admixing the active ingredients with liquid carriers, finely divided solid carriers, or both, and then shaping the product into the desired presentation if necessary. Disintegrants may be incorporated in solid dosage forms to facility rapid dissolution. Lubricants may also be incorporated to facilitate the manufacture of dosage forms (e.g., tablets).

3.2 Parenteral Dosage Forms

Parenteral dosage forms can be administered to patients by various routes including, but not limited to, subcutaneous, intravenous (including bolus injection), intramuscular, and intra-arterial. Because their administration typically bypasses patients' natural defenses against contaminants, parenteral dosage forms are specifically sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: water; aqueous vehicles such as, but not limited to, sodium chloride solution, Ringer's solution, and Dextrose; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

3.3 Transdermal, Topical and Mucosal Dosage Forms

Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences*, 18th eds., Mack Publishing, Easton Pa. (1990). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, penetration enhancers may be used to assist in delivering active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates may also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition

4. Kits

Also encompasses within the present disclosure is an article of manufacture or "kit," containing materials useful for the treatment or prophylaxis of a disease and/or disorder mediated by FPR1 in a subject.

In one embodiment, the kit comprises a container comprising the compound of the present disclosure. The kit is suitable for the treatment or prophylaxis of a disease and/or disorder mediated by FPR1, such as an immune disorder, an infectious disease, a cancer, a cardiovascular disease, or a trauma. Suitable containers include, for example, bottles, vials, syringes, blister pack, and etc. The container may be formed from a variety of materials such as glass, or plastic. The contain may hold a compound of the present disclosure or a pharmaceutical formulation thereof, in an amount effective for the treatment or prophylaxis of the disease and/or disorder mediated by FPR1, and may have a sterile access port, for example, the container may be an intravenous solution bag or a vail having a stopper pierceable by a hypodermic injection needle). The kit may further comprise a label or package insert on or associated with the container. The label or package insert indicates that the composition is used for treating condition of choice. Alternatively or additionally, the kit may further comprise a second container comprising a pharmaceutically acceptable buffer, such as a phosphate-buffered saline, Ringer's solution or dextrose solution. It may further include other materials desirable from a commercial and user standpoint, including other buffers, diluents, filters, needles, and syringes.

The kit may further include directions for the administration of the compound of the present invention and, if present, the second formulation for treating or preventing the disease and/or disorder mediated by FPR1. For example, if the kit comprises a first composition comprising the compound of the present disclosure, and a second pharmaceutical formulation, the kit may further include directions for the simultaneous, sequential, or separate administration of the first and second pharmaceutical compositions to a patient in need thereof.

In another embodiment, the kits are suitable for the delivery of solid oral forms of a compound of the present disclosure, such a kit includes, for example, a number of unit dosages. Such kits include card having the dosages oriented in the order of their intended use. An example of such kit is a "blister pack." Blister packs are well known in the packaging industry and are widely used for packaging pharmaceutical unit dosage forms. If desired, an aid may be provided, for example, in the form of numbers, letters, or other markings or with a calendar insert, designating the days in the treatment schedule in which the dosage can be administered.

According to one embodiment, the Kit may include, at least, (a) a first container containing the present compound of formula (I); and optionally, (b) a second container containing a second therapeutic agent that is any of a known FPR1 antagonist, an anti-inflammatory agent, an anti-biotic, an anti-neoplasm agent, or a cardiovascular drug; and (c) a legend associated with the kit for instructing a user how to use the kit. The legend may be in a form of pamphlet, tape, CD, VCD or DVD.

The present invention will now be described more specifically with reference to the following embodiments, which are provided for the purpose of demonstration rather than limitation. While they are typically of those that might be used, other procedures, methodologies, or techniques known to those skilled in the art may alternatively be used.

EXAMPLES

Materials and Methods
Neutrophil Preparation

Human neutrophils were obtained in lipopolysaccharide-free conditions by means of dextran sedimentation and Ficoll centrifugation.

Measurement of $O_2^{\cdot-}$ Production $O_2^{\cdot-}$ production was determined based on the SOD-inhibitable reduction of ferricytochrome c. Briefly, neutrophils ($6\times10^5$/mL) were treated with LS-PH at 37° C. at various concentrations (0.03 to 3 µM) for 5 min after being supplementing with 0.5 mg/mL ferricytochrome c and 1 mM $Ca^{2+}$. Cells were activated with formyl-L-methionyl-L-leucyl-L-phenylalanine (fMLF, 0.1 µM) for 10 min in the pre-process of cytochalasin B (CB, 1 µg/mL) for 3 min. Changes in absorbance with the reduction of ferricytochrome c at 550 nm were continuously monitored in a double-beam, six-cell positioner spectrophotometer with constant stirring (Hitachi U-3010, Tokyo, Japan). Calculations were based on the differences in the reactions with and without SOD (100 U ml$^{-1}$) divided by the extinction coefficient for the reduction of ferricytochrome c ($\epsilon$=21.1 mM$^{-1}$/10 mm).

Measurement of Elastase Release

MeO-Suc-Ala-Ala-Pro-Val-p-nitroanilide was employed as the elastase substrate for the determination of elastase release. Briefly, after supplementation with Methoxysuccinyl-Ala-Ala-Pro-Val-p-nitroanilide (Ms-Ala-Ala-Pro-Val-pNA) (100 µM), neutrophils ($6\times10^5$/mL) were equilibrated at 37° C. for 2 min and incubated with LS-PH at various concentrations for 5 min. Cells were activated with fMLF (0.1 µM) for 10 min in the pre-process of cytochalasin B (CB, 0.5 µg/mL) for 3 min, and changes in absorbance at 405 nm were continuously monitored to evaluate elastase release. Results are expressed as the percentage of elastase release in the drug-free control group, DMSO.

Measurement of ROS Release

After supplementation with dihydrorhodamine 123 (2 µM), neutrophils ($1\times10^6$/mL) were equilibrated at 37° C. for 12 min and incubated with LS-PH at various concentrations for 5 min. Cells were activated with fMLF (0.1 µM) for 5 min in the pre-process of cytochalasin B (CB, 0.5 µg/mL) for 3 min. Intracellular ROS was determined by use of flow cytometer.

Cell Viability Test

Cytotoxicity of LS-PH towards neutrophils was evaluated by measuring the level of lactate dehydrogenase (LDH) using a commercial kit (Promega). LDH is a cytosolic enzyme that is released only when cell membrane is disrupted (i.e., cell death), thus may be used as an indicator of cell viability. The kit measures a color change at ($\lambda$max=450 nm) when LDH reduces NAD to NADH. Cytotoxicity was expressed as the percent LDH activity obtained in cell-free medium compared to the total LDH activity. Total LDH activity was determined by lysing cells with 0.1% Triton X-100 for 30 min at 37° C.

FPR1 Binding Assay

Neutrophils ($2\times10^6$ cells/ml) were incubated with various concentrations of compound LS-PH (0.03 to 3 µM) or fMLF (10 µM) at 4° C. for 5 min, and labeled with FPR1-specific ligand FNLFNYK (4 nM) for 30 min. Then, the binding was determined by use of flow cytometry.

Statistical Analysis

Results are expressed as the mean±standard error of the mean (SEM), and comparisons were made using Student's t-test. A probability of 0.05 or less was considered significant. The software SigmaPlot was used for the statistical analysis.

Example 1 Isolation and Identification of Compound LS-PH ((E) 3,4-Seco-4(23), 20(29)-lupadiene-3,28-dioic acid)

(I)

The air-dried leaves and twigs of L. synbalanos (2.8 kg) was ground and extracted by MeOH at room temperature (15 L×3) to give a crude extract. This crude extract was partitioned between water and EtOAc to obtain two layers. The EtOAc layer was further partitioned with hexanes and 75% MeOH (aq). The 75% MeOH layer (123.4 g) was separated by a Si gel column eluting with hexanes/EtOAc/MeOH to furnish 9 fractions. Fraction 7 (17.0 g) was dissolved in $CH_2Cl_2$ to give a $CH_2Cl_2$ solvable portion fraction 7A. This fraction (1.1 g) was subjected to a LH-20 column eluting with MeOH/$CH_2Cl_2$=1:1 to yield a subfraction 7A1 (360.7 mg). Subfraction 7A1 was isolated by HPLC (Si, flow=2.0 mL/min, n-hexane/$CH_2Cl_2$/acetone=5:5:1) to give compound LS-PH (i.e., the compound of formula (I) (59.8 mg), which was confirmed by preparative TLC analysis.

$^1$H NMR (400 MHz, CDCl$_3$) δ4.73 (1H, br s, H-29), 4.61 (1H, br s, H-29), 4.84 (1H, br s, H-23), 4.65 (1H, br s, H-23), 1.72 (3H, s, H-30), 1.69 (3H, s, H-24), 0.99 (3H, s, H-26), 0.98 (3H, s, H-25), 0.83 (3H, s, H-27).

HRMS (MALDI-TOF) m/z 493.25 [M+Na]$^+$, $C_{30}H_{46}O_4$.

Figure 1:
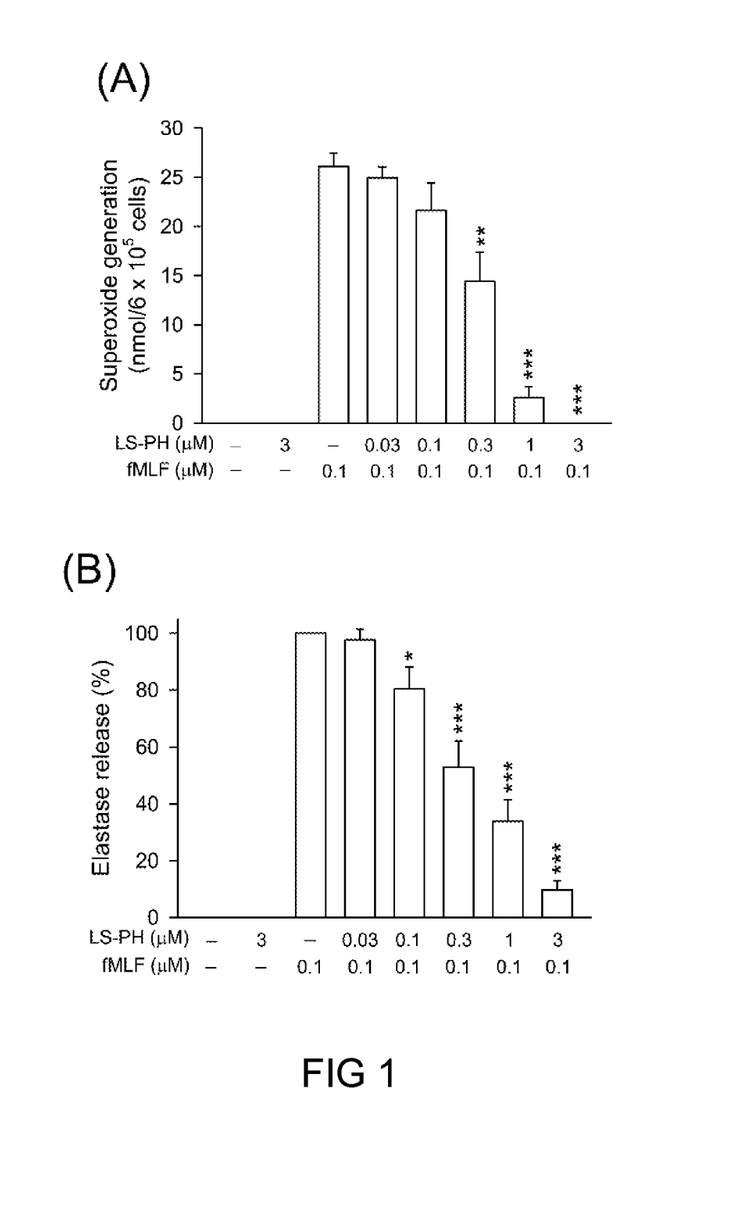
FIG. 1 illustrates the respective effects of compound LS-PH on (A) superoxide generation, and (B) elastase release in response to stimulation of fMLF in according to one embodiment of the present disclosure.
Figure 2:
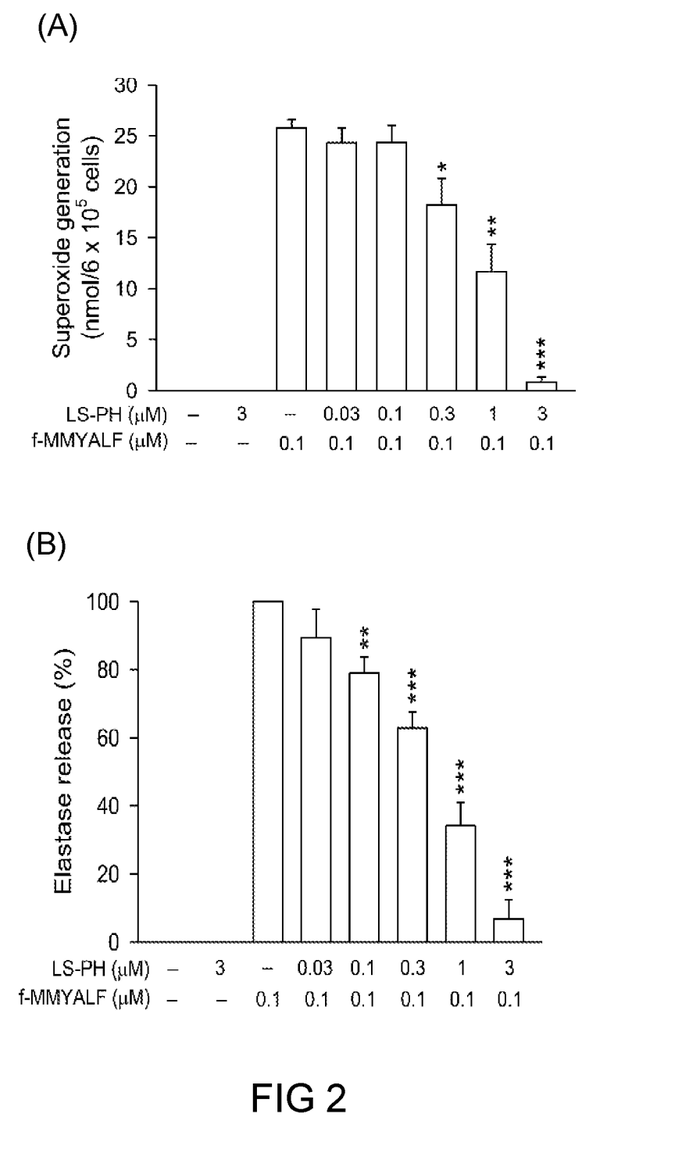
FIG. 2 illustrates the respective effects of compound LS-PH on (A) superoxide generation, and (B) elastase release in response to stimulation of f-MMYALF in accordance to one embodiment of the present disclosure.
Figure 3:
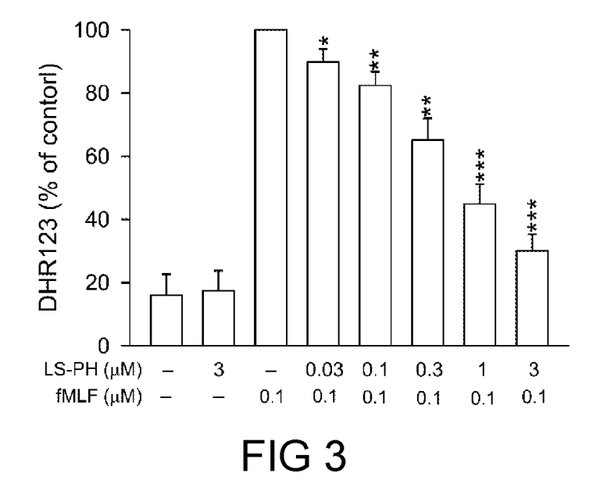
FIG. 3 illustrates the effect of compound LS-PH on intracellular ROS production in fMLF-activated human neutrophils in accordance to one embodiment of the present disclosure.

Example 2 Characterization of Compound LS-PH 2.1 Compound LS-PH Suppresses $O_2^{\cdot-}$ Production, Elastase Release and ROS Formation in Human Neutrophiles In this example, inhibitory effects of LS-PH on superoxide anion production, elastase release and ROS formation in human neutrophils were investigated, and results are depicted in FIGS. 1, 2 and 3, respectively.

As evident from FIG. 1, LS-PH was capable of suppressing superoxide production and elastase released from neutrophils in response to fMLF (FIGS. 1A and 1B), with $IC_{50}$ being about 0.26±0.11 µM and 0.71±0.18 µM, respectively. Similar results were found when another FPR1 agonist, f-MMYALF, was employed as the stimulant to active neutrophils (FIGS. 2A and 2B).

LS-PH was also found to suppress fMLF-induced intracellular ROS formation (FIG. 3) in human neutrophils.

2.2 Compound LS-PH does not Affect Cell Viability

Figure 4:
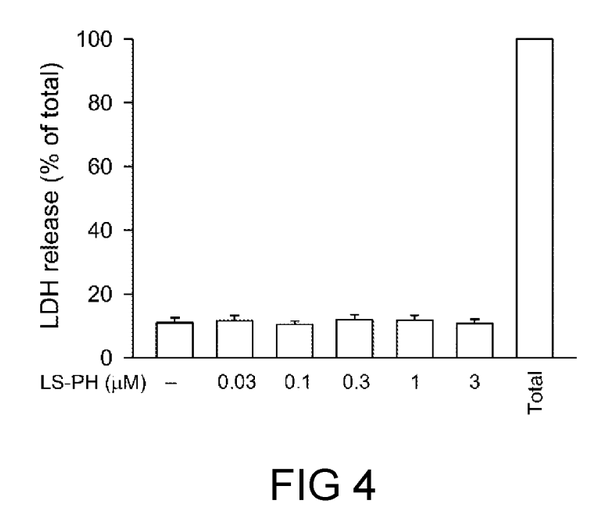
FIG. 4 illustrates the cytotoxicity of compound LS-PH on human neutrophils in accordance to one embodiment of the present disclosure.

The effect of compound LS-PH on cell viability was also investigated by comparing the respective levels of LDH released from neutrophils with or without the treatment of LS-PH, and results indicated that within the test concentrations (i.e., from 0.03 to 3 µM), compound LS-PH did not exhibit detectable cytotoxicity (FIG. 4).

2.3 Compound LS-PH Binds to Formyl Peptide Receptor 1 (FPR1)

Figure 5:
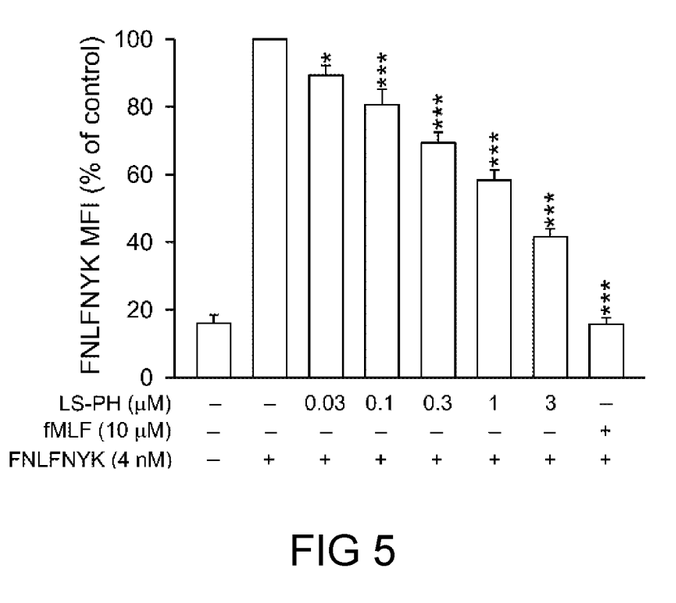
FIG. 5 illustrates the effect of compound LS-PH on the binding capability of FPR-specific ligand and FPR in accordance with one embodiment of the present disclosure.

To elucidate the action of compound LS-PH, the ability of compound LS-PH binding with FPR1 was investigated. Results are depicted in FIG. 5.

It was found that compound LS-PH at concentrations from 0.03 to 3 µM could significantly suppress the binding of another FPR1-specific ligand (i.e., FNLFNYK) with $IC_{50}$ about 1.72±0.35 µM, confirmed that compound LS-PH also acted through FPR1.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. A method for treating a disease and/or disorder mediated by a formyl peptide receptor 1 (FPR1) in a subject comprising administering to the subject a therapeutically effective amount of a compound of formula (I) or a pharmaceutically acceptable salt thereof, (I)

so as to ameliorate or alleviate the symptoms associated with the disease and/or disorder in the subject, wherein the disease and/or disorder mediated by FPR1 is bacterial infection, sepsis, psoriasis, and acute respiratory distress syndrome.

2. The method of claim 1, wherein the compound of formula (I) is administered to the subject in the amount of 0.01-100 mg/Kg.

3. The method of claim 1, wherein the subject is a human.

* * * * *